United States Patent [19]

Buchner

[11] 4,135,140
[45] Jan. 16, 1979

[54] ULTRASONIC IMAGING APPARATUS OPERATING ACCORDING TO THE IMPULSE-ECHO METHOD

[75] Inventor: Klaus Buchner, Uttenreuth, Germany

[73] Assignee: Siemens Aktiengesellschaft, Berlin & Munich, Germany

[21] Appl. No.: 804,495

[22] Filed: Jun. 8, 1977

[30] Foreign Application Priority Data

Jul. 2, 1976 [DE] Fed. Rep. of Germany ....... 2629942

[51] Int. Cl.² .......................... G01S 9/66; G01S 7/62
[52] U.S. Cl. ..................................... 340/1 R; 73/626; 73/628; 340/5 MP; 358/112; 358/140
[58] Field of Search .................. 340/1 R, 3 C, 5 MP; 73/625, 626, 628; 343/5 SC; 358/112, 140

[56] References Cited

U.S. PATENT DOCUMENTS

| | | | |
|---|---|---|---|
| 3,380,293 | 4/1968 | Murphy | 73/626 |
| 3,701,089 | 10/1972 | Cowan | 340/3 R |
| 3,790,925 | 2/1974 | Ahrens | 340/3 R |
| 4,010,466 | 3/1977 | Hofstein | 343/5 SC |
| 4,024,490 | 5/1977 | Wood | 340/3 R |

*Primary Examiner*—Richard A. Farley
*Attorney, Agent, or Firm*—Hill, Gross, Simpson, Van Santen, Steadman, Chiara & Simpson

[57] ABSTRACT

In the illustrated embodiment the ultrasonic applicator is activated to emit ultrasonic pulses along a plurality of scan lines simultaneously, the echo signals of all simultaneously scanned lines being stored and then rapidly read out during ultrasonic scanning along a further set of lines, the individual lines of each set being displayed in sequence and the successive sets being correspondingly displaced on the image screen so as to reproduce the ultrasonic image.

8 Claims, 3 Drawing Figures

ULTRASONIC IMAGING APPARATUS OPERATING ACCORDING TO THE IMPULSE-ECHO METHOD

BACKGROUND OF THE INVENTION

The invention relates to an ultrasonic imaging apparatus operating according to the impulse-echo method, intended particularly for medical diagnostics, comprising an ultrasonic applicator for the linear ultrasonic scanning of an examination subject and an image display device with a line generator for the reproduction of the echo impulses in the form of a line, as well as comprising an image generator for displacement of the line as a function of the displacement of the ultrasonic beam in the subject.

In the apparatus of this type, there is the problem of providing the highest possible number of scan lines in the ultrasonic echo image while simultaneously obtaining high image frequencies during the image reproduction. In the case of a good resolution of the echo image, there is then also a resulting image which is virtually free of flicker due to the relatively high image frequency.

SUMMARY OF THE INVENTION

It is an object of the present invention to disclose an ultrasonic imaging apparatus of the type initially cited which satisfies these requirements with the simplest technical means.

In accordance with the invention, the object is achieved by virtue of the fact that the ultrasonic applicator is constructed for the purpose of the chronologically successive linear ultrasonic scanning of the examination subject simultaneously in a plurality of scan lines lying at specific distances from one another which are always constant in their relative allocation, and that, after temporary storage, within the period of the transmit/receive cycle for the following line combinations, respectively, the echo signals of all simultaneously scanned lines are rapidly read-out, with the image-line spacings corresponding to the ultrasonic line spacings in the subject, onto the image display device for recording purposes.

In the apparatus according to the invention, while maintaining an unchanged normal basic timing rhythm of the transmit/receive cycles, solely on the basis of a simultaneously proceeding multiple scanning, an increased line scanning frequency results and thus also an increased image frequency in the case of a readout time of all echo impulses of a scan line formation, which readout time has been compressed into the receiving time of a single transmit/receive cycle. Thus, with a relatively high line number, the image frequency of the ultrasonic image representation is correspondingly increased by the simplest means.

Other objects, features and advantages of the present invention will be apparent from the following detailed description taken in connection with the accompanying sheets of drawings.

DETAILED DESCRIPTION

Figure 1:
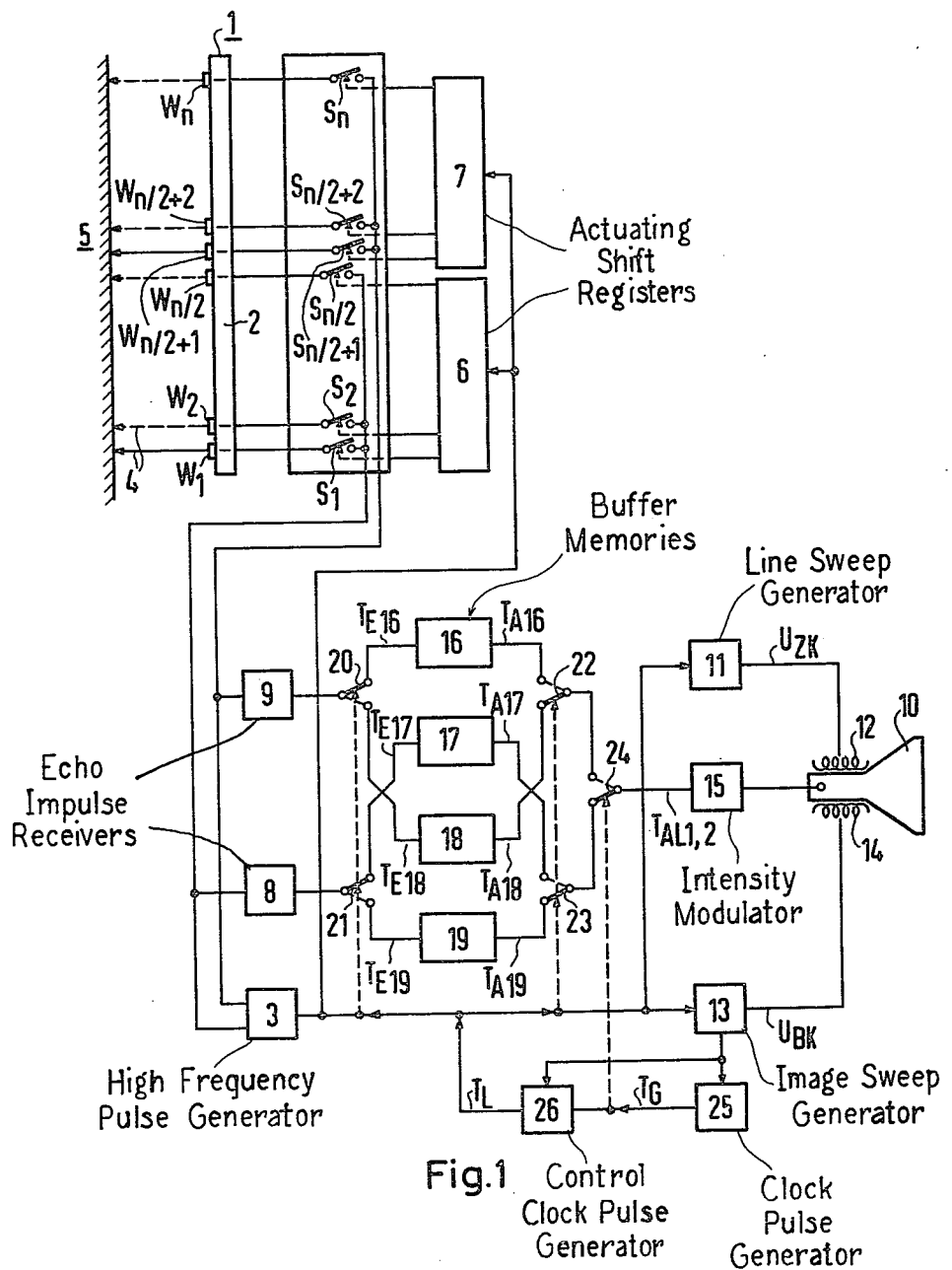
FIG. 1 illustrates an ultrasonic imaging apparatus according to the invention in a basic circuit diagram.

In FIG. 1, reference numeral 1 designates the ultrasonic applicator which, in the present instance, is constructed in the form of an ultrasonic array. Accordingly, applicator 1 consists of a plurality of ultrasonic transducers $W_1$ through $W_n$ (small piezoelectric crystal plates), which are supported adjacently of one another on a carrier section 2 of a material having good ultrasonic wave-attenuating properties. The individual transducer elements $W_1$ through $W_n$ can be selectively energized individually or in groups by means of high frequency pulses of a high frequency pulse generator 3 such that they radiate ultrasonic impulses in the direction of arrows 4 into an examination subject 5, e.g. a human body. Actuation of the individual transducer elements $W_1$ through $W_n$ in individual-or group-formation proceeds by means of an actuating mechanism comprising two actuating shift registers 6 and 7, as well as actuating switches $S_1$ through $S_n$ for the purpose of connecting transducer elements which are to be energized to the high frequency pulse generator 3 in the transmit mode and to a respective one of two echo impulse receiving amplifiers 8 and 9 in the receive mode. The basic circuit diagram according to FIG. 1 preferably operates with ultrasonic scanning in two scan lines simultaneously. For this reason, the switch bank of actuating switches $S_1$ through $S_n$ is subdivided into two groups of switches, the first of which, comprising switches $S_1$ through $S_{n/2}$, serving the purpose of actuating transducer elements or transducer element groups $W_1$ through $W_{n/2}$ specifically from the first half of the array, and the second group of switches, comprising switches $S_{(n/2) + 1}$ through $S_n$, serving the purpose of simultaneous actuation of transducer elements or transducer element groups $W_{(n/2) + 1}$ through $W_n$, specifically from the second half of the array. Accordingly, in the transmit mode, the switches of each switch group can be simultaneously and jointly supplied with the high frequency pulses of the single high frequency pulse generator 3. However, actuation of the two switch groups is shown as being effected by means of respective shift registers 6 and 7, and echo impulse reception proceeds separately for each switch group by means of the correspondingly assigned echo impulse receiving amplifier 8 or 9, respectively. In order to represent the echo signals, which are always received in chronological succession simultaneously from two ultrasonic scan lines, in the form of corresponding echo image lines, there is an electron beam tube 10, with which is coordinated in a conventional manner a line sweep generator 11 for the horizontal deflection coil 12, as well as an image sweep generator 13 for the vertical deflection coil 14 of the electron beam tube 10. Electron beam tube 10 further comprises an intensity modulator 15 for the purpose of intensity modulation of the image lines in the cadence of the echo impulses occurring. Reception and readout of echo signals of each line pair proceed in an alternating buffer memory operation such that the echo signals of two successive line pairs, in each instance, are alternately read into two buffer memory pairs 16 and 17, and 18 and 19, respectively, and are read out again from these memory pairs in a correspondingly alternating fashion. The read-in time of the parallel read-in of echo impulses of a line pair into a buffer memory pair 16, 17; 18, 19, respectively, essentially corresponds to the receiving time of these echo impulses from the examination subject 5. The chronologically successive readout of stored information of each buffer memory pair, however, proceeds at a higher frequency, preferably with half the duration of the read-in time. Storage and re-read-out of echo information with respect to the respective memory pairs proceed in the cadence of oscillatory switches 20, 21, at the input and oscillatory switches 22, 23 and 24, at the output of the memory pairs. Switches 20, 21, at the input, the switches 22, 23, at the output of the buffer memory pairs operate with the same frequency; however, they operate in counter rhythm operation. However, output switch 24 alternates with double the change-over switching frequency as compared to switches 20 through 23. In order to predetermine the change-over switching frequency for switch 24, there is a basic clock pulse generator 25 which is synchronized with image sweep generator 13. A control clock pulse generator 26 is provided as the clock pulse generator for predetermining the counter-rhythm change-over frequency of the switch pairs 20, 21, or 22, 23, as well as for predetermining the control clock pulse rate for the transmit/receive cycles of the ultrasonic applicator 1 and of the trigger pulses for the line sweep and also for the image sweep waveforms, respectively. In a preferred embodiment, this control clock generator 26 is a 2:1 division element which divides the basic clock rate $T_G$ of the basic clock pulse generator 25 to the half frequency rate $T_L = T_{G/2}$.

Figure 2:
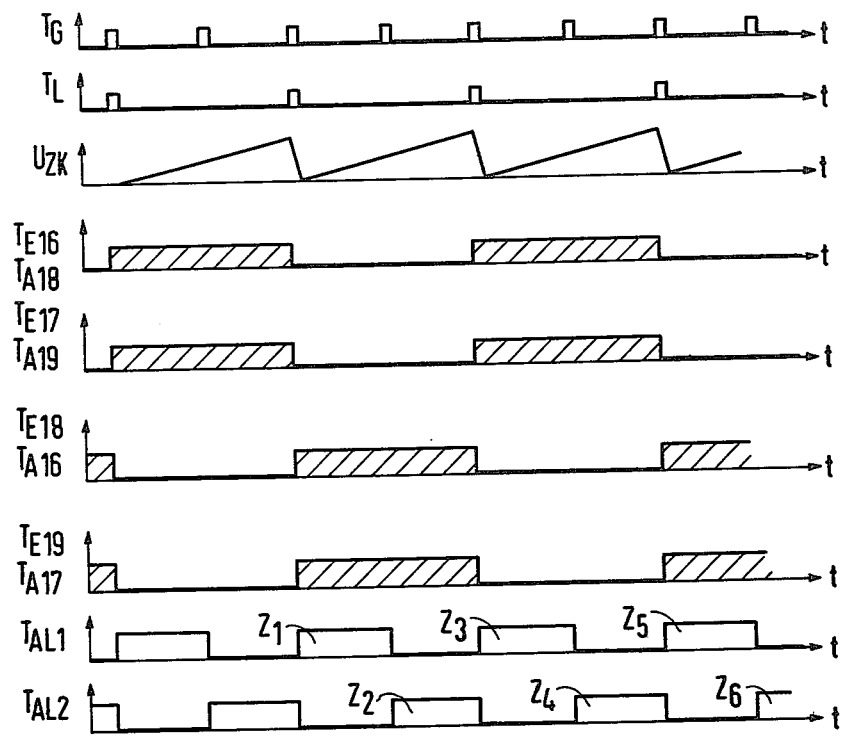
FIG. 2 illustrates a pulse diagram for explaining the operation of the apparatus of the basic circuit diagram according to FIG. 1.
Figure 3:
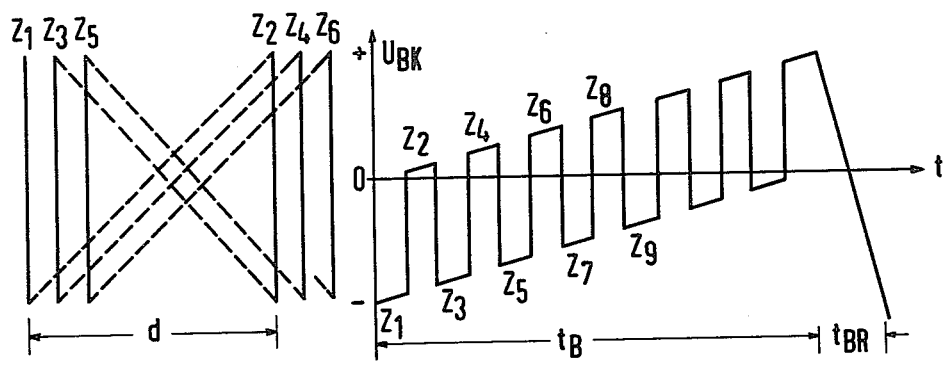
FIG. 3 illustrates a diagram of the line sweep and the associated image sweep voltage waveform at the image display device for the purpose of formation of an ultrasonic echo image in accordance with the invention.

The operational mode of the basic circuit diagram according to FIG. 1 is apparent in conjunction with the pulse and deflection diagrams of FIGS. 2 and 3, as follows:

In FIG. 1, switch 24 alternates its switching condition in the cadence of the basic clock pulses $T_G$ of basic clock pulse generator 25. In a corresponding fashion, with the control clock pulses $T_L$ of control clock pulse generator 26, there is a resulting alternating switch-over of the input switches 20 and 21, of memory pairs 16, 17 and 18, 19 which is in counter-rhythm to the output switches 22, 23. The control clock pulses $T_L$ further effect a simultaneous sequential through-pulsation of the register positions in shift registers 6 and 7. As a consequence, in each particular instance, always one (or more) switch (or switches) of the first switch-group, together with one (or more) associated switch (or switches) of the second group, are simultaneously closed in response to the advance pulsation of shift registers 6, 7. Since, in addition, with the occurrence of a control clock pulse $T_L$, the high frequency pulse generator 3 also produces a high frequency ultrasonic pulse, correspondingly associated transducer — or transducer group — pairs from the first and the second half of the array are simultaneously energized by way of respectively simultaneously closed switch-or switch sub-group-pairs, in order that ultrasonic radiation and thus ultrasonic scanning may proceed simultaneously in two ultrasonic lines. The echo impulses occurring simultaneously in each instance from each of these two scan lines are received in parallel formation for each scan line by receivers 8 and 9, and, in an alternating cadence relative to the following echo-line pair, are alternately stored in the one or the other buffer memory pair 16, 17 or 18, 19. Thus, in the instantaneous illustration of FIG. 1 (with individual transducer actuation per scan line), there takes place e.g. the storage of echo impulses of the scan line produced by transducer $W_1$ into memory 17, whereas the echo impulses of the additional ultrasonic line simultaneously scanned by transducer $W_{(n/2) + 1}$ are stored in memory 16. However, upon further pulsation into the following scan lines of the transducer pair $W_2$ and $W_{(n/2) + 2}$, with the simultaneously effected switch-over of switches 20 and 21, into the switching position illustrated in broken lines, storage of the echo information of these lines into memories 18 and 19 is brought about. However, during the period of storage of this information, there now proceeds a chronologically successive rapid scanning of the storage contents of memories 16 and 17 by way of the output switches 22 and 23 operated into the switching position illustrated by broken line, as well as by way of output switch 24 which is switched-over twice as rapidly. This operation is repeated correspondingly in alternating cadence for the following pairs of scan lines. Thus, in the rhythm of a progressive linear scanning of examination subject 5 in two scan lines simultaneously in each instance, echo information is alternately read in parallel formation into the memory pairs 16, 17, and 18, 19, and, in chronological succession, in the receiving time of the echo impulses of the following two scan lines, it is read out again with a doubled cadence in a corresponding alternating fashion. The alternating cadence of storage and re-read-out are clearly apparent from FIG. 2 on the basis of the illustrated switch-over pulse curves for the input and output clock pulses $T_{E16}$ through $T_{E19}$, and $T_{A16}$ through $T_{A19}$ of the individual memories 16 through 19 in conjunction with the read-out clock pulses $T_{AL1}$ or $T_{AL2}$, respectively, of output switch 24. The line echo information associated with the individual readout clock pulses are designated by $Z_1$, $Z_2$, $Z_3$, etc., corresponding to the sequence of their chronological occurrence at the display device. The respective line raster of the echo image recording on the image screen of the electron beam tube 10, which precisely corresponds spatially to that of the ultrasonic scanning in the examination subject, is illustrated to the left of FIG. 3. The spatial distance of respective associated scan or image reproduction lines of a line pair is designated therein by d, d being, in the embodiment of the invention according to FIG. 1, approximately equal to half the width of the display image screen; i.e., half the length of the ultrasonic array 1. The image sweep voltage $U_{BK}$, with which a line raster of this type can be realized in the simplest form, is illustrated in its chronological progression $U_{BK}(t)$ to the right in FIG. 3. The time period $t_B$ here denotes the time span of a sweep deflection of the image sweep across the image screen of the electron beam tube 2, whereas the time period $t_{BR}$ is the return time of the electron beam into the initial position after completion of an image sweep.

It will be apparent that many modifications and variations may be effected without departing from the scope of the novel concepts and teachings of the present invention.

I claim as my invention:

1. Ultrasonic imaging apparatus operating according to the impulse echo method, intended particularly for medical diagnostics, comprising an ultrasonic applicator for the linear ultrasonic scanning of an examination subject, and an image display device with a line generator for reproducing the echo pulses as lines and an image generator for the displacement of the line as a function of the displacement of the ultrasonic beam in the subject, characterized in that the ultrasonic applicator has control means constructed for the purpose of a linear ultrasonic scanning of the examination subject simultaneously in a plurality of scan lines during each transmit/receive cycle, lying at specific distances from one another, the allocation of spacing between simultaneously active scan lines in successive transmit/receive cycles being always constant, and buffer storage means for storing the echo signals of all simultaneously scanned lines and for rapid readout thereof, the control means providing for image line spacings at the display device corresponding to the ultrasonic line spacings in the subject, for the purpose of recording the readout echo signals of the simultaneously scanned lines on the image display device within the period of the transmit/receive cycle of the following line combinations.

2. Ultrasonic imaging apparatus according to claim 1, characterized in that reception and readout of the echo signals of a line combination with respect to the buffer storage means proceed in an alternating buffer memory operation, the buffer storage means comprising a plurality of buffer memories such that the echo signals of two successive line combinations, are alternately read into respective sets of said buffer memories and in the following instance, are read out again from the respective sets of memories in a corresponding alternating fashion.

3. Ultrasonic imaging apparatus according to claim 2, characterized in that the sum of the readout times of the successive reading out of all the line information of a line combination corresponds approximately to the read-in time of the parallel read-in of a line combination into the buffer memories.

4. Ultrasonic imaging apparatus according to claim 1, characterized in that the ultrasonic applicator has control means constructed for the purpose of ultrasonic scanning of the examination subject in two scan lines-simultaneously during each transmit/receive cycle.

5. Ultrasonic imaging apparatus according to claim 4, characterized in that, with the ultrasonic applicator comprising a plurality of adjacently disposed transducer elements, there is coordinated with the transducer elements of one-half of the array a first group of actuating switches, and there is coordinated with the transducer elements of the additional half of the array a second group of actuating switches, whereby, in each of a continuous sequence of cycles, there is always only one switch or one switch sub-group of each switch-group closed for the purpose of simultaneous excitation of two transducer elements or transducer element groups which are allocated to a specific distance between said two scan lines.

6. Ultrasonic imaging apparatus according to claim 5, characterized in that the control means comprises a shift register functioning as a switching pulse generator and coordinated with each switch-group for the purpose of a continuous sequencing of switches of the one switch-group together with corresponding switches of the other switch-group.

7. Ultrasonic imaging apparatus according to claim 5, characterized in that there is commonly coordinated with each switch-group one single high frequency pulse generator.

8. Ultrasonic imaging apparatus according to claim 7, characterized in that an echo signal receiver, respectively, is separately coordinated with each switch-group.

* * * * *